United States Patent
Golestanirad et al.

(10) Patent No.: US 9,526,890 B2
(45) Date of Patent: Dec. 27, 2016

(54) ELECTRODE DESIGNS FOR EFFICIENT NEURAL STIMULATION

(71) Applicant: Sunnybrook Research Institute, Toronto (CA)

(72) Inventors: Laleh Golestanirad, Brookline, MA (US); Simon J. Graham, Toronto (CA)

(73) Assignee: SUNNYBROOK RESEARCH INSTITUTE, Toronto, Ontario (CA)

( * ) Notice: Subject to any disclaimer, the term of this patent is extended or adjusted under 35 U.S.C. 154(b) by 0 days.

(21) Appl. No.: 14/683,323

(22) Filed: Apr. 10, 2015

(65) Prior Publication Data

US 2015/0209577 A1    Jul. 30, 2015

Related U.S. Application Data

(63) Continuation of application No. PCT/CA2013/000871, filed on Oct. 10, 2013.

(60) Provisional application No. 61/712,420, filed on Oct. 11, 2012.

(51) Int. Cl.
*A61N 1/05* (2006.01)
*A61N 1/04* (2006.01)

(52) U.S. Cl.
CPC ........... *A61N 1/0551* (2013.01); *A61N 1/0456* (2013.01); *A61N 1/0534* (2013.01); *A61N 1/0587* (2013.01); *A61N 1/05* (2013.01); *A61N 1/0565* (2013.01)

(58) Field of Classification Search
CPC .................................................. A61N 1/0551
See application file for complete search history.

(56) References Cited

U.S. PATENT DOCUMENTS

| | | | |
|---|---|---|---|
| 5,609,611 A | | 3/1997 | Bolz et al. |
| 6,127,977 A | * | 10/2000 | Cohen ............ H01Q 1/36 343/700 MS |
| 6,140,975 A | | 10/2000 | Cohen |
| 6,292,703 B1 | | 9/2001 | Meier et al. |

(Continued)

FOREIGN PATENT DOCUMENTS

WO    2014056090    4/2014

OTHER PUBLICATIONS

Butson et al., "Sources and effects of electrode impedance during deep brain stimulation," Clinical neurophysiology, vol. 117, pp. 447-454, 2006.

(Continued)

*Primary Examiner* — Eric D. Bertram
(74) *Attorney, Agent, or Firm* — Bereskin & Parr LLP/S.E.N.C.R.L., s.r.l.

(57) ABSTRACT

Electrodes for use in neural stimulation applications, shaped to have fractal or pseudo-fractal geometries, with a generally planar core portion of the electrode using a base fractal geometry. A series of successively smaller holes is provided in the core portion, where each hole in the generally planar core portion can have a perimeter shape that is self-similar to a perimeter shape of the generally planar core portion. The selected electrode geometry affects the spatial distribution of the electric field in neuron-bearing tissue. This spatial distribution is related to the irregularity—or non-uniformity—of current density on the electrode surface. Optimized electrode geometries increase the efficiency of neural stimulation by maximizing the spatial variation of current density on the electrode surface.

22 Claims, 13 Drawing Sheets

(56) References Cited

U.S. PATENT DOCUMENTS

| | | | |
|---|---|---|---|
| 7,221,981 B2 | 5/2007 | Gliner | |
| 7,453,401 B2 | 11/2008 | Jow | |
| 7,715,921 B2* | 5/2010 | Palti | A61N 1/0408 607/115 |
| 7,750,856 B2 | 7/2010 | Cohen | |
| 8,275,455 B2 | 9/2012 | Shippy et al. | |
| 2007/0112402 A1 | 5/2007 | Grill et al. | |
| 2011/0301683 A1* | 12/2011 | Axelgaard | A61N 1/0452 607/149 |
| 2012/0209350 A1 | 8/2012 | Taylor et al. | |

OTHER PUBLICATIONS

Butson et al., "Tissue and electrode capacitance reduce neural activation volumes during deep brain stimulation," Clinnical neurophysiology, vol. 116, pp. 2490-2500, 2005.

Canavero et al., "Extradural motor cortex stimulation for advanced Parkinson disease," Journal of neurosurgery, vol. 97, pp. 1208-1211, 2002.

Deharo et al., "Pacemaker longevity. Replacement of the device," Ann Cardiol Angeiol (Paris), vol. 54, pp. 26-31, 2005.

Falconer, Fractal geometry: mathematical foundations and applications: John Wiley & Sons, 2003.

Fregni et al., "Transcranial direct current stimulation of the unaffected hemisphere in stroke patients," Neuroreport, vol. 16, p. 1551, 2005.

Fregni et al., "Treatment of major depression with transcranial direct current stimulation," Bipolar disorders, vol. 8, pp. 203-204, 2006.

Geddes et al., "Criteria for the Selection of Materials for Implanted Electrodes", Annals of Biomedical Engineering, vol. 31, pp. 879-890, 2003.

Golestanirad et al., "Analysis of Fractal Electrodes for Efficient Neural Stimulation", Frontiers in Neuroengineering, vol. 6, Article 3, Jul. 12, 2013, pp. 1-10.

Gould et al., "Complications associated with implantable cardioverter-defibrillator replacement in response to device advisories," Journal of the American Medical Association, vol. 295, p. 1907, 2006.

Grill, "Electrical stimulation for control of bladder function," in Engineering in Medicine and Biology, 2009, pp. 2369-2370.

Hines et al., "Neuron: a tool for neuroscientists," The Neuroscientist, vol. 7, pp. 123-135, 2001.

Huang et al., "Modulation effects of epidural spinal cord stimulation on muscle activities during walking," Neural Systems and Rehabilitation Engineering, IEEE Transactions on, vol. 14, pp. 14-23, 2006.

Jaggard, "Fractal electrodynamics and modeling," Directions in electromagnetic wave modeling, pp. 435-446, 1991.

Jaggard, "Fractal electrodynamics: wave interactions with discretely self-similar structures," C. Baum and H. Kritikos Electromagnetic Symmetry.—Washington DC: Taylor and Francis Publishers, pp. 231-261, 1995.

Kleiner-Fisman et al., "Motor cortical stimulation for parkinsonism in multiple system atrophy," Archives of neurology, vol. 60, p. 1554, 2003.

Liebetanz et al., "Anticonvulsant Effects of Transcranial Direct-current Stimulation (tDCS) in the Rat Cortical Ramp Model of Focal Epilepsy," Epilepsia, vol. 47, pp. 1216-1224, 2006.

Logé et al., "A novel percutaneous technique to implant plate-type electrodes," Minimally Invasive Neurosurgery, vol. 54, pp. 219-222, 2011.

Mandelbrot, The Fractal Geometry of Nature: Macmillan, 1983.

McIntyre et al., "Uncovering the mechanism(s) of action of deep brain stimulation: activation, inhibition, or both," Clinical neurophysiology, vol. 115, pp. 1239-1248, 2004.

Mond et al., "The Steroid-Eluting Electrode: A 10-Year Experience," Pacing and Clinical Electrophysiology, vol. 19, pp. 1016-1020, 1996.

Mono et al., "The Electrode-Tissue Interface: The Revolutionary Role of Steroid Elution," Pacing and Clinical Electrophysiology, vol. 15, pp. 95-107, 2006.

Nitsche et al., "Excitability changes induced in the human motor cortex by weak transcranial direct current stimulation," J. Physiol., vol. 527, pp. 633-639, 2000.

Petersen et al., "The Effect of Steroid Elution on the Performance of Coronary Sinus Leads for Left Ventricular Pacing in Dogs," Progress in Biomedical Research, vol. 9, pp. 41-44, 2004.

Ranck, "Specific impedance of rabbit cerebral cortex," Experimental neurology, vol. 7, pp. 144-152, 1963.

Rasche et al., "Motor cortex stimulation for long-term relief of chronic neuropathic pain: a 10 year experience," Pain, vol. 121, pp. 43-52, 2006.

Rattay, "Analysis of models for extracellular fiber stimulation," IEEE transactions on bio-medical engineering, vol. 36, pp. 676-682, 1989.

Werner et al., "An overview of fractal antenna engineering research," Antennas and Propagation Magazine, IEEE, vol. 45, pp. 38-57, 2003.

Wongsampigoon et al., "Computational modeling of epidural cortical stimulation," Journal of neural engineering, vol. 5, p. 443, 2008.

Yousif et al., "Investigating the depth electrode—brain interface in deep brain stimulation using finite element models with graded complexity in structure and solution," Journal of neuroscience methods, vol. 184, pp. 142-151, 2009.

Document relating to PCT Application No. PCT/CA2013/000871, dated Apr. 17, 2014 (International Search Report).

Document relating to PCT Application No. PCT/CA2013/000871, dated Apr. 23, 2015 (International Preliminary Report on Patentability and Written Opinion).

Golestanirad et al., "Analysis of Fractal Electrodes for Efficient Neural Stimulation", 35th Annual International conference of the IEEE EMBS, Osaka, Japan, Jul. 2013.

Engelhard et al., "Electrodes for Bioelectric Signals Sensing and Stimulation", 2009, Friedrich-Alexander-University, Erlangen-Nuremberg, Germany.

Johnson, "Fractal Electrodes for Retinal Implants: Highlight", Integrative Graduate Education and Research Traineeship, retrieved from <http://www.igert.org/highlights/521>, dated Nov. 21, 2011.

Ostrovsky, "Fractal Nanoflowers May Improve Retinal Prostheses", retrieved from <http://www.medgadget.com/2011/05/fractal_nanoflowers_may_improve_retinal_prostheses.html>, dated May 9, 2011.

Schaldach, "Fractal Coated Leads: Advanced Surface Technology for Genuine Sensing and Pacing", Department of Biomedical Engineering, Jun. 2000, pp. 259-272, Germany.

Wei et al., "Analysis of High-Perimeter Planar Electrodes for Efficient Neural Stimulation", Frontiers in Neuroengineering, vol. 2, Article 15, Department of Biomedical Engineering, Duke University, Nov. 10, 2009, pp. 1-10.

\* cited by examiner

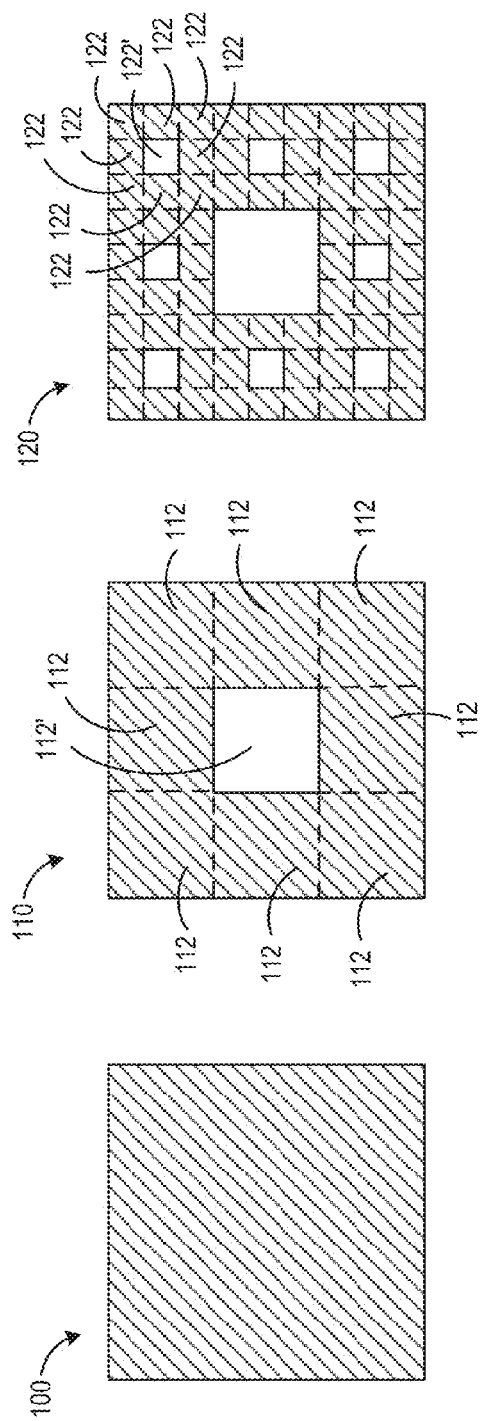

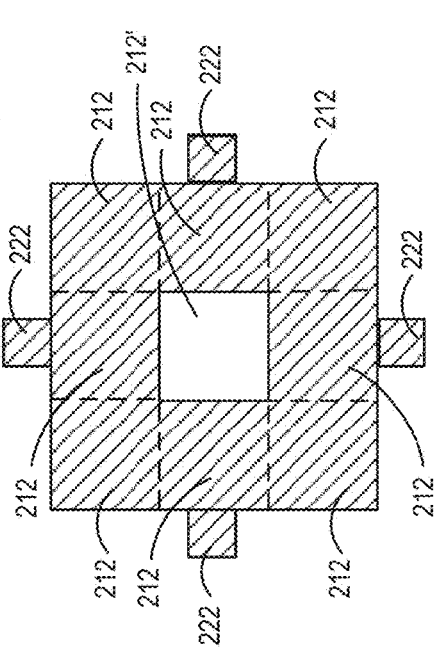
FIG. 2B
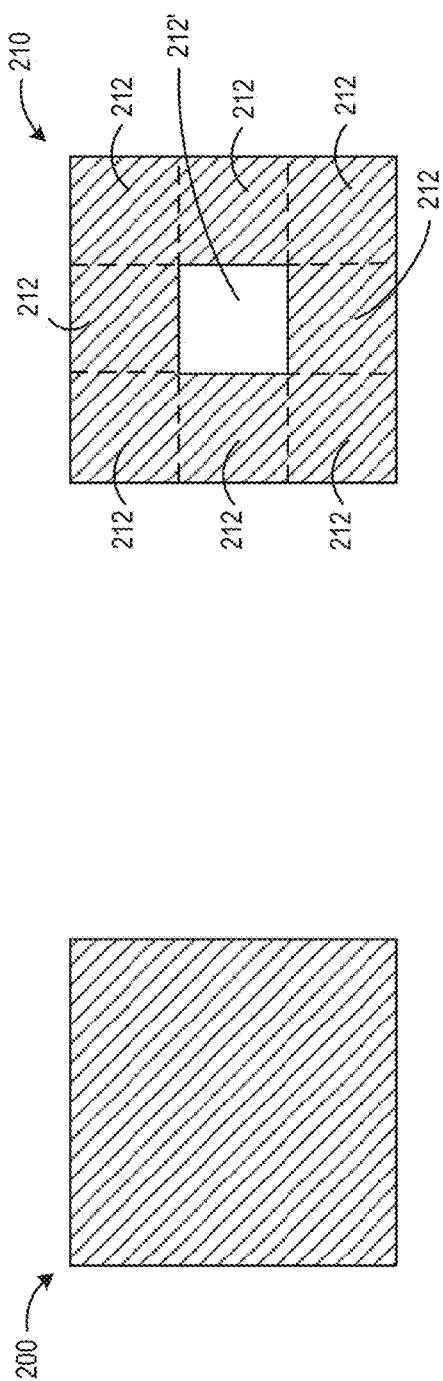
FIG. 2D
FIG. 2A
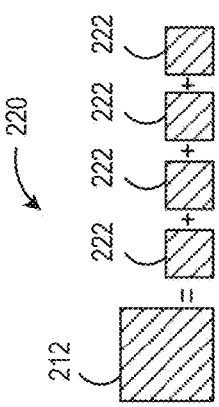
FIG. 2C

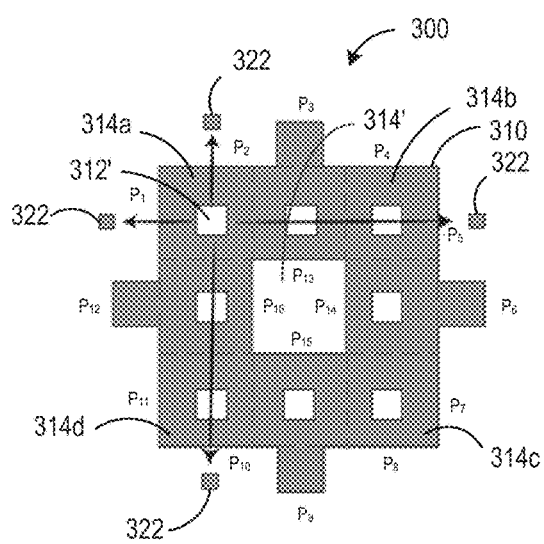
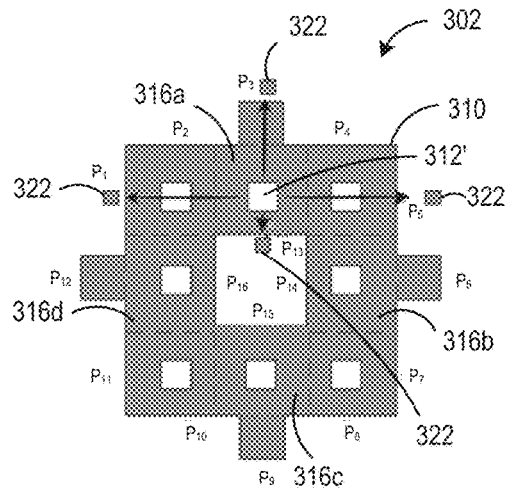
FIG. 3A  FIG. 3B
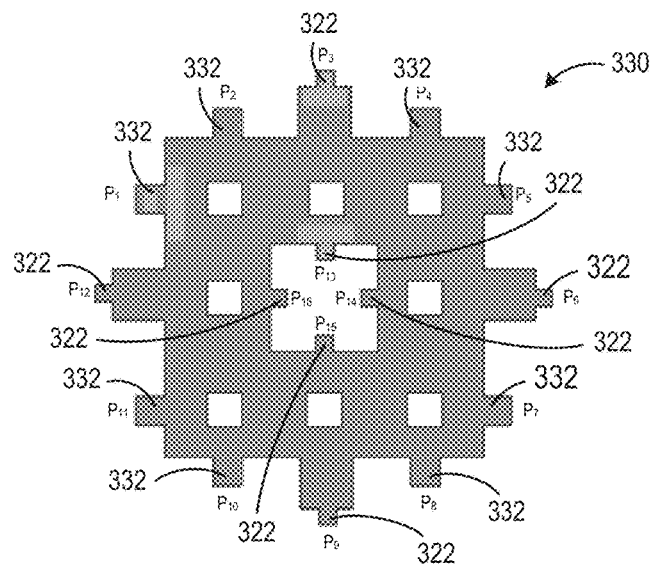
FIG. 3C

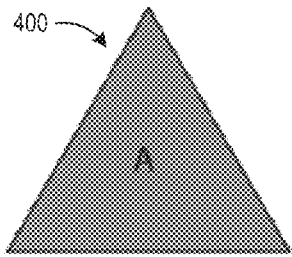
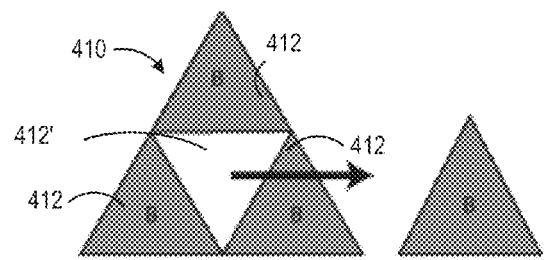
FIG. 4A　　　　　　　　　FIG. 4B
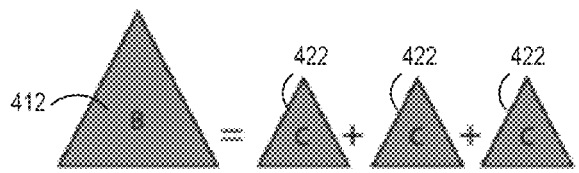
FIG. 4C
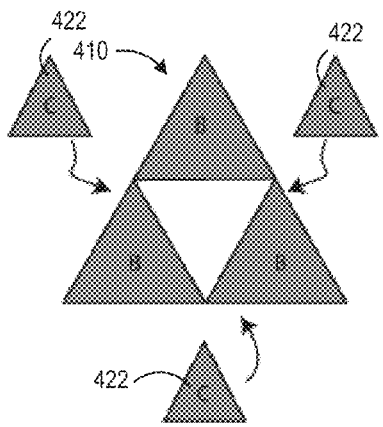
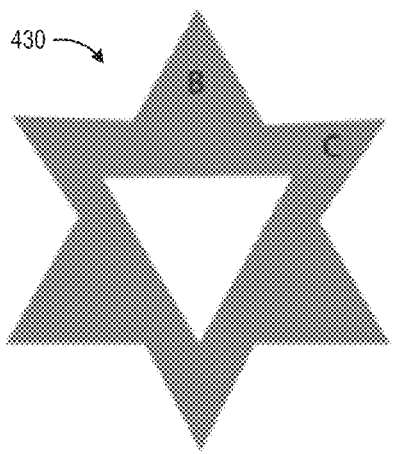
FIG. 4D　　　　　　　　　FIG. 4E

ELECTRODE DESIGNS FOR EFFICIENT NEURAL STIMULATION

CROSS-REFERENCE TO RELATED PATENT APPLICATIONS

This application is a continuation of International Patent Application No. PCT/CA2013/000871, filed on Oct. 10, 2013, which claims the benefit of U.S. Provisional Patent Application No. 61/712,420, filed on Oct. 11, 2012. The complete disclosure of each of International Patent Application No. PCT/CA2013/000871 and U.S. Provisional Patent Application No. 61/712,420 is incorporated herein by reference.

FIELD

The described embodiments relate to electrodes for electrical stimulation of organic tissue and, in particular, to neural stimulation electrodes.

BACKGROUND

Electrical stimulation of the nervous system is a technique used for restoring function to individuals with various diseases or impairments. Planar electrodes in particular are being increasingly used in neuro-stimulator devices for stimulating the central and peripheral nervous systems in humans.

Epidural spinal cord stimulation (ESCS), for example, includes electrical stimulation to the dorsal roots and/or the dorsal columns of the spinal cord. ESCS can be used for treating pain associated with various syndromes. Recently the combination of ESCS and partial weight bearing therapy has been shown to induce significant functional gains in the over-ground gait of individuals with chronic, incomplete spinal cord injury and with very low motor scores in their lower limbs.

Epidural cortical stimulation (ECS) is used in the brain for transferring electrical stimulation via planar electrodes for therapeutic applications. ECS can be used for the treatment of a variety of disorders, such as neuropathic pain, movement disorders, Parkinson's disease, and stroke rehabilitation.

Another application of electrical stimulation of the nervous system is transcranial direct current stimulation (tDCS). tDCS is a non-invasive, painless, safe and portable technique that has been found to modulate cortical excitability. The tDCS procedure is simple and economical—that is, the procedure is an injection of a weak DC current (less than 2 mA) between the surface electrodes that are connected to a stimulation device. tDCS has also shown promising results as a potential therapy in stroke, Parkinson's disease, depression and epilepsy. The advantages of tDCS, along with its positive results, reinforce its applicability within the clinical practice.

Planar electrodes are also used in electrical stimulation for restoring and/or improving control of bladder functions. In cases of neurological diseases, for example, promising results have been shown in the restoration of continence and micturition.

Deep brain stimulation (DBS) is another application of electrical stimulation of the nervous system. DBS involves high frequency electrical stimulation of the thalamic or basal ganglia structures (e.g., subthalamic nucleus (STN) or an internal segment of the globus pallidus) for the treatment of movement disorders. DBS is rapidly emerging as an alternative to surgical lesions.

The most widely used medical implanted electrodes are those used in artificial cardiac pacemaker devices to apply electric currents to the muscles of the human heart. The primary purpose of these devices is to maintain an adequate pace and rhythm of the heart's contractions. These devices have been used since the 1960s in millions of patients around the world.

SUMMARY

In a broad aspect, there is provided an electrode for neural stimulation, the electrode comprising: an electrically conductive body, the body having a generally planar core portion, wherein the generally planar core portion has a plurality of holes therein, and wherein the plurality of holes has one or more internal perimeters.

In some cases, each of the one or more internal perimeters comprises at least three edges and at least three vertices, each edge being joined to its adjacent edges at a respective one of the at least three vertices. In some cases, the at least three edges define a non-180° angle at each vertex in the at least three vertices.

In some cases, respective edges and vertices of the plurality of holes are configured to reduce a capacity dimension of a surface of the core portion to less than 2.

In some cases, each of the one or more internal perimeters comprise at least twelve edges and at least twelve vertices. In some cases, the plurality of holes form a Sierpinski triangle of at least order 2.

In some cases, each of the one or more internal perimeters comprise at least thirty-six edges and at least thirty-six vertices. In some cases, the plurality of holes form a Sierpinski square of at least order 2.

In some cases, each of the plurality of holes has a perimeter shape that is self-similar to a perimeter shape of the generally planar core portion.

In some cases, the generally planar core portion has a base shape that corresponds to a regular polygon having n sides. In some cases, n is at least three. In some cases, n is at least four.

In some cases, a shape of the generally planar core portion is obtainable from a base shape that corresponds to a regular polygon having n sides by removing a first order smaller regular polygon having n sides from the interior of the base shape to provide a first order hole in the plurality of holes, the first order hole having n edges. In some cases, the shape is further obtainable by removing a plurality of k-th order smaller regular polygons having n sides from the interior of the base shape to provide a plurality of k-th order holes in the plurality of holes, each of the plurality of k-th order holes having n edges. In some cases, the shape is further obtainable by repeatedly removing the plurality of k-th order smaller regular polygons for two or more integer values of k. In some cases, the shape is further obtainable by dividing an area of the first order smaller regular polygon into a plurality of second order smaller regular polygons having n sides, and attaching the second order smaller regular polygons to one or more selected edges of the shape. In some cases, the shape is further obtainable by dividing an area of each of the plurality of k-th order smaller regular polygons to provide (k+1)-th order smaller regular polygons having n sides, and attaching the (k+1)-th order smaller regular polygons to an edge of the shape.

In some cases, n is at least three. In some cases, n is at least four. In some cases, n is at least 20, and the generally planar core portion approximates a closed curve in shape.

In some cases, k is between 2 and 5. In some cases, k is between 3 and 5.

In some cases, the generally planar core portion forms a closed curve in shape, and wherein each of the plurality of holes forms a closed curve in shape. In some cases, a shape of the generally planar core portion is obtainable from a base shape that corresponds to a closed curve by removing a first order smaller closed curve from the interior of the base shape to provide a first order hole in the plurality of holes. In some cases, the shape is further obtainable by removing a plurality of k-th order smaller closed curves from the interior of the base shape to provide a plurality of k-th order holes in the plurality of holes. In some cases, the shape is further obtainable by repeatedly removing the plurality of k-th order smaller dosed curves for two or more integer values of k.

In some cases, the generally planar core portion is curved.

In some cases, the generally planar core portion is flexible.

In another broad aspect, there is provided an electrode for neural stimulation, the electrode comprising: an electrically conductive body, the body having a core portion for increasing a neural activation function in a tissue, at a distance of 5 mm from a surface of the electrode, wherein an absolute value of the neural activation function is increased between 2 and 10 times relative to a solid surface electrode of equivalent area.

In some cases, the neural activation function is increased in a direction orthogonal to the surface of the electrode.

In some cases, the electrode is an ESCS electrode. In some cases, the electrode is an ECS electrode. In some cases, the electrode is a tDCS electrode. In some cases, the electrode is a DBS electrode. In some cases, the electrode is a cardiac pacemaker electrode.

BRIEF DESCRIPTION OF THE DRAWINGS

A preferred embodiment of the present invention will now be described in detail with reference to the drawings, in which:

FIGS. 1A to 1E illustrate a fractal shape of various orders, in accordance with several embodiments;

FIGS. 2A to 2D illustrate a first order modified fractal shape;

FIGS. 3A to 3C illustrate a second order modified fractal shape, based on the first order modified fractal shape;

FIGS. 4A to 4G illustrate modified triangle fractal shapes of various orders;

DETAILED DESCRIPTION

Figure 4F:
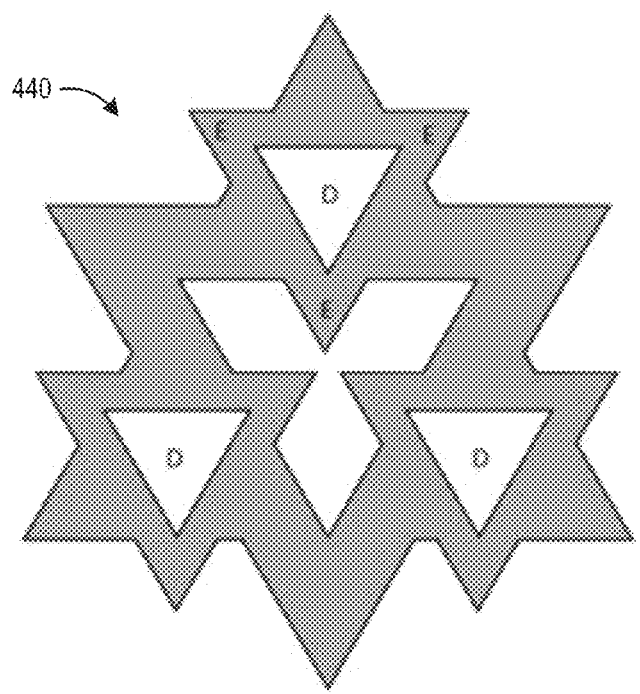

It will be appreciated that for simplicity and clarity of illustration, where considered appropriate, reference numerals may be repeated among the figures to indicate corresponding or analogous elements or steps. In addition, numerous specific details are set forth to provide a thorough understanding of the exemplary embodiments described herein. However, it will be understood by those of ordinary skill in the art that the embodiments described herein may be practiced without these specific details. In other instances, well-known methods, procedures and components have not been described in detail since these are known to those skilled in the art. Furthermore, it should be noted that this description is not intended to limit the scope of the embodiments described herein, but rather as merely describing one or more exemplary implementations.

As described above, significant effort in the art has been focused on finding optimal anatomical targets for different nerve stimulation techniques. Prior attempts at increasing the efficiency of electrical stimulation have primarily focused on the development of new materials for reducing stimulation thresholds. For example, steroid-eluting electrodes have been used for suppressing inflammation and accordingly, enhancing the electrical contact at the tissue-electrode interface. The usage of a new material for implanted electrodes may require thorough, time-consuming and expensive testing, validation and regulatory approval on the basis of biocompatibility, sterility, short and long-term toxicity, and mechanical durability.

Generally, electrical stimulation of the nervous system involves the use of electrodes powered by pulse generators (PGs). These pulse generators can be either external to the body, or surgically implanted pulse generators (IPGs). IPGs generally use primary cell batteries and typically require surgical replacement when the battery is depleted. Surgical replacement can be expensive and can carry substantial risk of complications. In one study, the complication rate associated with the replacement of cardiac pacemakers was found to be three times higher than that for the original placement of the device (J. C. Deharo and P. Djiane, "Pacemaker longevity: Replacement of the device," Ann Cardiol Angeiol (Paris), vol. 54, pp. 26-31, 2005). In another study, the complication rate associated with the replacement of implanted defibrillators was found to be 81% (P. A. Gould and A. D. Krahn, "Complications associated with implantable cardioverter-defibrillator replacement in response to device advisories," Journal of the American Medical Association, vol. 295, p. 1907, 2006).

There is a need for neuro-stimulator devices that can provide electrical stimulation of the nervous system, while operating at reduced power levels, or with increased efficiency, or both.

As described above, conventional nerve stimulation techniques have been focused on finding optimal anatomical targets. Conventional electrodes are generally limited to square- or circular-shaped conductors configured individually or in array formations.

However, efficiency of nerve stimulation can be enhanced through the use of novel electrode shapes, configurations of the electrodes, or both.

The particular shape (e.g., geometric design) of an electrode can have a substantial role in controlling the activation or excitation of populations of neurons in the vicinity of the electrode. In particular, electrode geometry can affect the spatial distribution of the electric field in the tissue comprising the neurons and, consequently, the pattern of neural excitation can also be affected. This spatial distribution is related to the irregularity—or non-uniformity—of current density on the electrode surface. Accordingly, optimized electrode geometries can be used to increase the efficiency of neural stimulation by maximizing the spatial variation of current density on the electrode surface.

By increasing the efficiency of an electrode, the power requirements of an IPG that powers the electrode can be reduced, and the working lifetime of the IPG battery can therefore be extended. As a result, both the cost and risk associated with repeated IPG replacement surgeries can be reduced. Furthermore, reduced power requirements can facilitate use of smaller batteries and accordingly, the use of smaller-sized IPGs. Smaller IPGs can be more convenient for both surgeons and patients, as they can be more easily implanted and tolerated by patients.

Generally, the electrodes described in the present application can be used for neural stimulation. However, in some embodiments, the electrodes may be used for electrical stimulation of other biological tissue.

Generally, the electrodes may have an electrically conductive body with a generally planar core portion. The generally planar core portion may be configured in shapes with one or more internal (inner) or external (outer) perimeters, or both, which serve to increase variations in current density on the electrode surface, and thereby improve neural activation. In some examples, the generally planar core portion may have one or more holes that can be created by removing portions from an interior of the generally planar core portion.

In some embodiments, each of the holes may have an internal perimeter with at least three edges and at least three vertices. Each edge may be joined to its adjacent edge at one of the vertices so that the edges define a non-0°, non-180° angle at each vertex. In some variant embodiments, a large number of edges and vertices, for example twenty or more, may be provided to approximate a closed curve. In some cases, the number of edges and vertices may be about 50, or about 100.

In some other embodiments, the generally planar core portion may be configured with shapes that form a closed curve in shape, such as a circle, ellipse or ovoid, for example.

In some embodiments, each hole may be configured in a shape with a perimeter that is self-similar to that of the generally planar core portion.

In designing the electrode shape or geometry, a neural activation function ($f$) may be considered. Maximization of the neural activation function generally results in a corresponding increase in the efficiency of neural excitation by the electrode.

The neural activation function is generally proportional to a second spatial derivative of the extracellular potential, $V_e$. This neural activation function can be written in terms of the electric field E and the electric current J as shown in Equation (1) below:

$$f \propto \frac{\partial^2 V_e}{\partial z^2} = -\frac{\partial (E_z)}{\partial z} = -\frac{1}{\sigma}\frac{\partial (J_z)}{\partial z} \quad (1)$$

where z is a direction along an axon and generally orthogonal to a surface of the electrode, and σ is the specific conductivity of the medium.

As shown in Equation (1), the neural activation function is proportional to the first spatial derivative of the electric field in the direction of the axon.

One way of altering the geometries of planar electrodes for maximizing the neural activation function is to increase an internal or external perimeter of the electrode. However, conventionally, increases in perimeter are tied to increases in overall surface area of the electrode, which can be impractical and unsuitable for certain applications.

Another related way of altering electrode geometry to maximize the neural activation function is to increase the number of discontinuities in a perimeter of the electrode. That is, by increasing the number of vertices—and, correspondingly, the number of edges—that make up the perimeter. A larger number of "sharper" angles tends to increase the activation function.

More generally, the neural activation function may be maximized by increasing an irregularity of a current profile on a surface of the electrode, since the neural activation function is generally proportional to the spatial derivative of the electric field. This irregularity can be achieved by the approaches outlined above, such as increasing the number of perimeter discontinuities and lengthening perimeter. It is noteworthy that the activation function along an axis perpendicular to the surface of a planar electrode can be increased by these irregularities in the plane of the electrode. The irregularities in the current in the plane of the electrode lead to irregularities in the fields perpendicular to the electrode.

The irregularity of a surface current profile can be quantified with a metric defined here as topological edginess. The topological edginess metric can be characterized by a number of edges and holes that are located in a surface, or generally planar portion, of an electrode.

Certain fractal shapes may exhibit a useful amount of topological edginess for use in neural stimulation electrodes.

Such fractals can be generally described as a fragmented geometric shape that can be split into successively smaller parts. Each part may appear to be a reduced-size copy of the whole, that is, each part is self-similar to the whole.

Fractals may also be characterized by a metric known as fractal dimension or capacity dimension. Fractal dimension is a metric that can quantify the complexity of fractal shapes. The fractal dimension can characterize fractal patterns, or sets, by quantifying their complexity as a ratio of the change in detail to the change in scale. For sets describing ordinary geometric shapes, for example, the fractal dimension is the Euclidean, or topological, dimension, and is typically an integer value. That is, the fractal dimension for sets describing points is 0, the fractal dimension for sets describing lines is 1, the fractal dimension for sets describing surfaces is 2 and the fractal dimension for sets describing 3-dimensional geometries is 3.

Unlike topological dimensions for ordinary geometric shapes, the fractal dimension can have non-integer values, which can indicate that a fractal set fills space in a quantitatively different fashion than an ordinary geometrical set.

Also, idealized fractal geometries can theoretically have an infinite perimeter while maintaining a finite area. This large perimeter (and corresponding large number of vertices) relative to a small area thus provides a basis for neural stimulation electrodes. In practice, fractal shapes may be limited to a predetermined order (for example, a fifth order) due to manufacturing constraints. That is, in a fifth order pattern, a fractal geometric pattern may be repeated at successively smaller sizes up to five times.

In the field of radio-frequency communication, fractal electrodynamics combines the use of fractal geometry with electromagnetic theory to develop improved designs for controlling the radiation pattern, wave propagation and scattering characteristics of radio-frequency devices, typically at frequencies in the MHz and GHz range.

However, fractal geometries have not been used to control static electric field distribution in tissue (e.g., for neural stimulation).

As noted above, fractal geometries can maximize the irregularity of a current profile on their surface and consequently, in the adjacent tissue. The resulting neural activation function can therefore also be maximized.

Such fractal or pseudo-fractal geometries can be achieved in electrodes by configuring the generally planar core portion of an electrode using a base fractal geometry, and providing a series of successively smaller holes in the core portion, wherein each hole in the generally planar core portion can have a perimeter shape that is self-similar to a perimeter shape of the generally planar core portion.

These geometries can be further enhanced or modified to provide additional perimeter irregularities. For example, planar electrodes with a generally planar portion configured in a shape of a modified fractal will generally have a reduced capacity dimension (thus, increasing the topological edginess of the electrode) while maintaining a generally equivalent amount of current that can be delivered to the tissue. Finite element analysis of field distribution in conjunction with simulations of a large neuron population have shown that these enhanced, modified fractal-shaped electrodes can produce a significantly higher neural activation function that leads to up to 22% reduction in the input power consumption, while maintaining the same percentage of neural activations as compared to conventional, solid electrodes.

Generally, fractal-shaped or irregular perimeter planar electrode designs can be implemented with existing manufacturing techniques and materials and do not require exhaustive biocompatibility testing typically required of new implanted medical materials. Implanted materials should exhibit a suitable tissue response, allergic response, electrode-tissue impedance and radiographic visibility, as described for example in "Criteria for the Selection of Materials for Implanted Electrodes", L. A. Geddes and R. Roeder, Annals of Biomedical Engineering, vol. 31, pp. 879-890, 2003. Examples of such materials include gold, platinum, platinum-iridium, tungsten and tantalum. Insulating materials may include polyimide and glass. However, in some embodiments, the described electrodes could be formed of new materials in order to further maximize the efficiency of stimulation.

Many different types, or families, of fractal geometries may be used as the shape of the generally planar portion of the electrode. For example, the fractal geometries may be based on a Sierpinski square (also sometimes called a Sierpinski carpet), a Sierpinski triangular gasket, or the like. Other types of fractal geometries may also be used.

For example, the generally planar core portion of an electrode may have a base shape that corresponds to a regular polygon with a number of sides n. In some embodiments, n may be at least three. In some other embodiments, n may be at least four.

The shape of the generally planar core portion may be obtained from the base shape by removing a first order smaller regular polygon with the number of sides n from an interior of the base shape. As a result, a first order hole is provided in the generally planar core portion. In the self-similar case, the first order hole also has n edges, although in some embodiments, the number of edges may vary if self-similarity is not maintained. This shape of the generally planar core portion with one first order hole is defined herein as a first order fractal shape.

In some further embodiments, the shape of the generally planar core portion may be further modified by removing one or more k-th order smaller regular polygons with, for example, n sides from the interior of the base shape and, as a result, providing corresponding k-th order holes, k may be a set of integer values greater than or equal to two. In the self-similar case, each of the k-th order holes has n edges. The shape of the generally planar core portion may also be obtained by successively and repeatedly removing multiple k-th order smaller regular polygons for each integer value of k between 2 and the desired order. The resulting shape is defined herein as a k-order fractal shape.

In some example embodiments, the value of k may be between 2 and 5, and preferably between 3 and 5. Larger values of k are generally possible, but may be limited by manufacturing constraints and diminishing returns associated with successive miniaturization of each larger order. Features on the electrode which are substantially smaller than the size of the targeted neurons may have little if any effect, and can be avoided for the sake of simplified construction.

The design of an example neural stimulation electrode with a shape based on the Sierpinski carpet fractal shape is now described with reference to FIGS. 1A to 1E.

Referring now to FIGS. 1A to 1E, there are illustrated electrodes demonstrating a Sierpinski carpet fractal shape for various orders (e.g., values of k).

FIG. 1A illustrates a base square electrode 100, which may be a starting point for the design of the Sierpinski carpet shape.

Continuing now to FIG. 1B, there is illustrated a first order, or first stage, fractal shape 110. As shown in FIG. 1B, the fractal shape 110 is based on the base square 100 of FIG. 1A, itself divided into nine congruent first order squares, or sub-squares 112. That is, the base square 100 can be considered as a 3×3 grid structure. To obtain the first order fractal shape 110, the sub-square 112 in the center of fractal shape 100 is removed or omitted, such that a first order center hole 112' is defined within the fractal shape 110. Accordingly, the first order fractal shape 110 has an internal perimeter formed by the first order center hole 112', consisting of four edges each joined to an adjacent edge at one of four vertices. In the particular example of a square or rectangular shape, each vertex generally defines a 90° angle.

As described with reference to FIGS. 1C to 1E, the first order fractal shape 110 of FIG. 1B can be further modified to obtain higher-order fractal shapes.

Referring now to FIG. 1C, a second order, or second stage, fractal shape 120 is illustrated, which can be based on the first order fractal shape 110 of FIG. 1B. To obtain the second order shape 120, the process of obtaining fractal shape 110 from fractal shape 100 can be repeated for each of the eight sub-squares 112 of fractal shape 110. That is, each first order sub-square 112 of second order shape 120 can be further divided into a smaller 3×3 grid to define eight second order squares 122 and a central second order hole 122'. It will be understood that, although reference numerals are only shown for one sub-square 112 of fractal shape 120 in FIG. 1C, these reference numerals can similarly be applied to the other seven sub-squares 112 of fractal shape 120.

Figure 10:
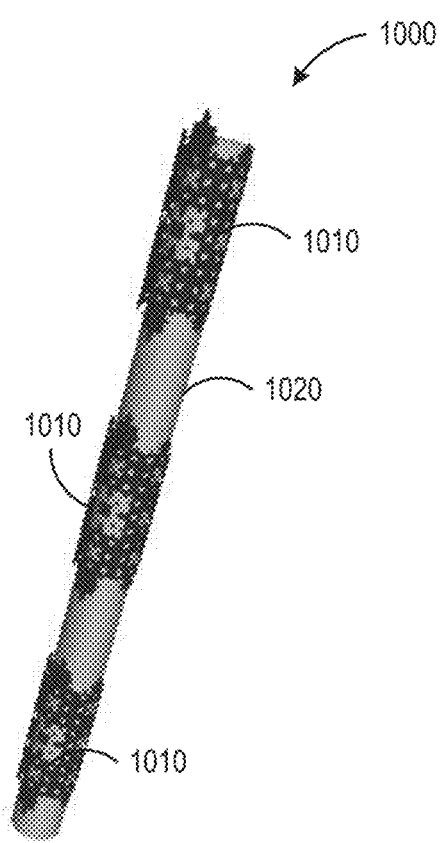
FIG. 10 is a cylindrical electrode with modified fractal shape in accordance with an example embodiment.

As illustrated in FIG. 10, the second order fractal shape 120 has a cumulative internal perimeter formed by the first order center hole 112' and the eight second order center holes 122'. The cumulative internal perimeter, therefore, comprise thirty-six edges each joined to an adjacent edge at one of the thirty-six vertices. Each vertex generally defines a 90° angle.

Accordingly, in some embodiments, the cumulative internal perimeter of the holes in the generally planar core portion may comprise at least thirty-six edges and at least thirty-six vertices. In such embodiments, the resulting fractal shape of the electrode may be an equivalent second order Sierpinski square.

The above-described process of dividing sub-squares into further smaller sub-squares and removing a central portion can be repeated to generate higher-order fractal shapes. For example, FIGS. 1D and 1E illustrate third- and fourth-order fractal shapes 130, 140 respectively. However, further higher-order fractal shapes may also be generated in this manner.

FIGS. 1A to 1E are related to the design of a Sierpinski carpet fractal shape. However, other fractal shapes, such as a Sierpinski triangle shape, may be designed and constructed using a similar process.

Accordingly, in embodiments based on the Sierpinski triangle, the cumulative internal perimeter of the holes in the generally planar core portion of a second-order fractal shape may comprise at least twelve edges and at least twelve vertices.

As described herein, a capacity dimension can be determined from a ratio of a change in detail to a change in scale. For the Sierpinski carpet fractal shape described with reference to FIGS. 1A to 1E, a fractal dimension can be defined by Equation (2):

$$d_{capacity} = -\lim_{k \to \infty} \frac{\ln N_k}{\ln L_k} \quad (2)$$

where $N_k$ is a number of sub-squares in the $k^{th}$ order; and $L_k$ is a length of a side of a hole in the $k^{th}$ order.

For ease of exposition, it will be assumed that the base shape 100 of FIG. 1A has a unit area equal to one, and $A_k$ is a fractional area of remaining sub-squares in the $k^{th}$ order. For k>0, the values of $N_k$, $L_k$ and $A_k$ can be determined as:

$$N_k = 8^k$$

$$L_k = 3^{-k}$$

$$A_k = L_k^2 N_k = \left(\frac{8}{9}\right)^k$$

Accordingly, the ratio $$\frac{\ln N_k}{\ln L_k}$$

for the Sierpinski carpet fractal shape of FIGS. 1A to 1E, for large values of k, asymptotically approaches the capacity dimension, which is:

$$d_{capacity} = -\lim_{k \to \infty} \frac{\ln N_k}{\ln L_k} = 1.892789 \cdots$$

Fractal dimensions are often determined empirically using a graphical approach whereby a regression line is estimated for some measure of size or structure and some measure of scale, according to a definition such as that given in Equation (2), with the two measures represented on a log-log plot.

Accordingly, the capacity dimension of the Sierpinski carpet fractal shape of FIGS. 1A to 1E is less than two. Since, as described above, a fractal dimension of 2 indicates a solid surface, a capacity dimension value of less than two indicates that the topological edginess of the geometry of the Sierpinski carpet fractal shape of FIGS. 1A to 1E has been increased.

Accordingly, the topological edginess and perimeter irregularity of an electrode can be increased with the use of fractal shapes. In particular, the edges and vertices of the holes in an electrode may be configured so that a surface of the generally planar core portion of the electrode has a capacity dimension of less than 2.

As higher-order fractal shapes are employed, the total conductive surface area of an electrode may be reduced. This may have a negative impact on the efficiency of neuron excitation, since the total current delivered to the tissue may be reduced.

To counteract this effect, modified shapes based on the above-described fractal shapes may be provided. Modified fractal shapes may be designed according to the above-described approach of removing or omitting portions of the electrode. However, in contrast to the electrodes of FIGS. 1A to 1E, the surface area of each removed or omitted portion may be "re-attached" at an external or internal perimeter of the electrode. Correspondingly, total surface of the area of the electrode may be maintained at a generally constant value, while the topological edginess or perimeter irregularity (due to the increased number of discontinuities and vertices) may be further enhanced.

In one example, based on the first order fractal shape 110 of FIG. 1B, the shape of the generally planar core portion may be further modified by dividing an area of the first order smaller regular polygon (i.e., the removed central portion 112') into one or more second order smaller regular polygons, where a collective area of the second order smaller regular polygons is substantially equivalent to the area of the first order smaller regular polygon. Each of the second order smaller regular polygons may have n sides and may then be re-attached or re-included to selected internal or external perimeters of the shape. The value of n may be at least 3 (e.g., for triangle-based shapes) and may be higher. The resulting fractal shape may be generally referred to as a first order modified fractal shape.

In some further embodiments, the process may be repeated for successive shape orders. That is, the shape of the generally planar core portion may be further modified by dividing an area of multiple k-th order smaller regular polygons to provide (k+1)-th order smaller regular polygons. Each of the (k+1)-th order smaller regular polygons may have n sides and may be attached to an internal or external perimeter or edge of the shape. The resulting fractal shape may be generally referred to as a k-th order modified fractal shape.

The value of n may be at least 3 and is preferably between 3 and 5. For modified fractal shapes, the value of k may be between 2 and 5, and preferably between 3 and 5.

The design of an example neural stimulation electrode with a shape based on the modified fractal shape is now described with reference to FIGS. 2A to 2D.

FIG. 2A illustrates a base square electrode 200, which may be a starting point for the design of the modified fractal shape. Base square electrode 200 has a surface area A.

Continuing now to FIG. 2B, there is illustrated a first order Sierpinski fractal shape 210, corresponding to fractal shape 110 of FIG. 1B. As shown in FIG. 2B, the fractal shape 210 is based on the base square 200 of FIG. 2A, and is divided into eight congruent first order squares or sub-squares 212 and has a central sub-square that is removed or omitted to define a first order center hole 212'. The first order center hole 212' has an equivalent area B that is equal to one-ninth of the surface area A.

In some embodiments, four congruent second order squares 222 may be provided, each having a surface area C, which is equal to one-quarter of the equivalent area B, as illustrated in FIG. 2C. In other embodiments, fewer or more second order squares 222 may be provided, however their combined area should substantially equal B. In some embodiments, polygons other than a square may be used if self-similarity to the base shape is not maintained.

Each second order square 222 may then be "re-attached" to the first order fractal shape 210 of FIG. 2B along an external perimeter, to provide a first order modified fractal shape 230, as shown in FIG. 2D. As shown in FIG. 2D, the second order squares 222 have been included at center points of the external perimeter edges. However, other attachment points are possible.

It should be noted that although the design of the electrode is described in terms of removing and re-attaching portions of the electrode material, this is for convenience and ease of description only. The electrode shapes described herein may be—and preferably are—constructed from a monolithic material, for example by etching, photolithography, or cutting from a sheet material using a die in the desired shape.

As with the fractal shapes of FIGS. 1A to 1E, higher-order modified fractal shapes can be obtained similarly by repeating the remove-and-reattach design approach, as described herein with reference to FIGS. 2A to 2D.

Design of a second order modified fractal shape is now described with reference to FIGS. 3A to 3C.

A second order modified fractal shape is generally based on a first order modified fractal shape, such as shape 230 of FIG. 2D. Shape 230 has a center hole 212' defined by sub-squares 212.

As shown in each of FIGS. 3A and 3B, a second order center hole 312' can be provided in each of the eight sub-squares 314 of shape 300, the sub-squares 314 corresponding to sub-squares 212 of FIG. 2D. The second order center hole 312' has a surface area of D that can be equal to one-ninth of the area B as defined by center hole 212' of shape 230 and 314'.

Similarly as shown in FIG. 2C, each of the removed second order squares corresponding to each second order center hole 312' may be further divided into, for example, four congruent third order squares 322. Each third order square 322 can therefore have a surface area E that is equal to one-quarter of the surface area D. In other embodiments, fewer or more third order squares 322 may be provided, however their combined area should substantially equal D. In some embodiments, polygons other than a square may be used if self-similarity to the base shape is not maintained.

Each of the third order squares 322 may then be "re-attached" to the second order modified fractal shape 310 along an internal or external perimeter, to provide a second order modified fractal shape.

In the illustrated examples of FIGS. 3A to 3C, different positions along the outer and inner perimeters of the second order Sierpinski fractal shape 310 are labelled with position labels $P_1$ to $P_{16}$.

In FIG. 3A, an example configuration for reattaching the third order squares 322 to one or more perimeters of the second order Sierpinski fractal shape 310 is shown. For ease of exposition, squares located in a corner position are labelled as 314a, 314b, 314c, and 314d, respectively.

As shown in FIG. 3A, each of the four third order squares 322 corresponding to the second order center hole 312' located in the corner square 314a may be reattached at different positions located on one or more perimeters, such as the positions labelled $P_1$, $P_2$, $P_5$, and $P_{10}$.

Similarly, the third order squares 322 corresponding to the second order center hole 312' in the corner square 314b may be reattached at the positions $P_1$, $P_4$, $P_5$, and $P_8$. The third order squares 322 corresponding to the second order center hole 312' in the corner square 314c may be reattached at the positions $P_4$, $P_7$, $P_8$, and $P_{11}$. Likewise, the third order squares 322 corresponding to the second order center hole 312' in the corner square 314d may be reattached at the positions $P_2$, $P_7$, $P_{10}$, and $P_{11}$.

Referring now to FIG. 3B, another example configuration for reattaching the third order squares 322 to one or more perimeters of the second order modified fractal shape 310 is shown. For ease of exposition, each square located in an interior (i.e., non-corner) position is labelled as 316a, 316b, 316c, and 316d, respectively.

As shown in FIG. 3B, each of the four third order squares 322 corresponding to the second order center hole 312' located in the middle square 316a may be reattached at different positions located on a perimeter, such as the positions labelled $P_1$, $P_3$, $P_5$, and $P_{13}$. Similarly, the third order squares 322 corresponding to the second order center hole 312' in the middle square 316b may be reattached at the positions $P_4$, $P_6$, $P_8$, and $P_{14}$; the third order squares 322 corresponding to the second order center hole 312' in the middle square 316c may be reattached at the positions $P_{15}$, $P_7$, $P_9$, and $P_{11}$; and the third order squares 322 corresponding to the second order center hole 312' in the middle square 316d may be reattached at the positions $P_{16}$, $P_{10}$, $P_{12}$, and $P_2$.

It will be appreciated that, according to the methodology outlined above, two or more third order squares 322 may be positioned at a single position, such as position $P_1$. In such cases, rather than attach each third order square 322 individually, the area of each square 322 to be positioned may be combined to produce a larger square 332.

Reference is now made to FIG. 3C, which illustrates an example of a second order modified fractal shape 330.

Second order modified fractal shape 330 is the resulting shape from repeating the process described with reference to FIGS. 3A and 3B.

As shown in FIG. 3C, each of the reattached portions 332 located at each of the $P_1$, $P_2$, $P_4$, $P_5$, $P_7$, $P_8$, $P_{10}$ and $P_{11}$ positions can be provided by combining, or merging, three third order squares 322 together. Each of the reattached portions 332 may have a surface area F, which is three times the surface area E. Each of the reattached portions 322 located at the $P_3$, $P_6$, $P_9$, $P_{12}$, $P_{13}$, $P_{14}$, $P_{15}$, and $P_{16}$ positions, however, may retain a surface area E.

In some embodiments, this recombination of subsquares 322 to form combined subsquares 332 may be omitted, and each subsquare may be reattached at an arbitrary position. In other embodiments, other subsquares may be combined to reduce the number of attachment positions.

Moreover, for higher-order modified fractal shapes, there is a corresponding increase in degree of freedom for attachment positions. It will be appreciated that other configurations for reattaching portions of removed areas may be used for building a modified fractal shape. In some embodiments, one configuration for reattaching the portions may be consistently used throughout a construction of a modified fractal. In some other embodiments, more than one configuration for reattaching the portions may be used in a sequential or alternating fashion during the construction of the modified fractal.

It will be understood that the above process of constructing modified fractals as described with FIGS. 2A to 2D and FIGS. 3A to 3C may be applied to other fractal geometries, such as a modified fractal shape based on the Sierpinski triangle, or the like.

Referring now to FIGS. 4A to 4G, there are illustrated modified triangle fractal shapes of various orders.

FIG. 4A illustrates a base triangle electrode 400, which may be a starting point for the design of the modified fractal shape. Base triangle electrode has a surface area A.

Continuing now to FIG. 4B, there is illustrated a first order fractal shape 410. As shown in FIG. 4B, the fractal shape 410 is based on the base triangle 400 of FIG. 4A, and is divided into three congruent first order triangles or sub-triangles 412 and has a central sub-triangle that is removed or omitted to define a first order center hole 412'. The first order center hole 412' has an equivalent area B that is equal to one-fourth of the surface area A.

In some embodiments, three congruent second order triangles 422 may be provided, each having a surface area C, which is equal to one-third of the equivalent area B, as illustrated in FIG. 4C. In other embodiments, fewer or more second order triangles 422 may be provided, however their combined area should substantially equal B. In some embodiments, polygons other than a triangle may be used if self-similarity to the base shape is not maintained.

Each second order triangle 422 may then be "re-attached" to the first order fractal shape 410 of FIG. 4B along an external perimeter as shown in FIG. 4D, to provide a first order modified fractal shape 430, as shown in FIG. 4E. As shown in FIGS. 4D and 4E, the second order triangles 422 have been positioned at center points of the external perimeter edges. However, other attachment points are possible.

In some embodiments, higher order modified fractal shapes may be obtained by repeating the methodology described above; that is, removing a portion of the generally planar core portion to provide a hole and "re-attaching" equivalent area portions elsewhere on the core portion.

Figure 4G:
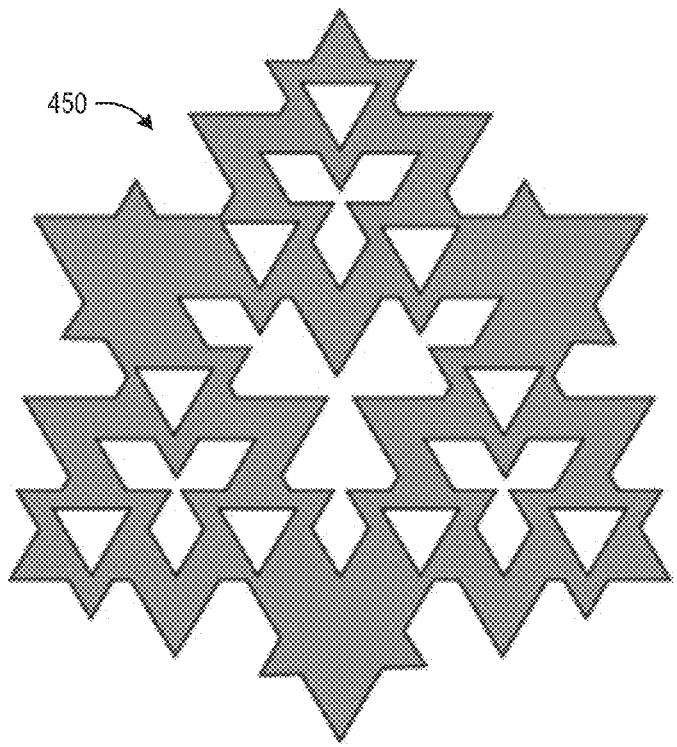

Referring now to FIGS. 4F and 4G, there are illustrated third and fourth order modified fractal shapes 440 and 450, respectively, each based on a triangle base shape.

To investigate the performance of fractal shaped electrodes, three-dimensional finite element models (FEM) of the fractal electrodes can be simulated inside a three-dimensional homogenous conducting medium. An example finite element model may include a planar electrode surface with a potential of −1 V and a homogenous volume conductor representing neural tissue, such that the conductor has a conductivity of 0.2 S/m. The tissue adjacent to the fractal electrode may be modelled as a cylindrical shape with a diameter of 10 cm and a height of 10 cm. For simulating a cathodic monopolar stimulation, a potential of 0 V may be associated with the outer boundary of the cylindrical shape.

In one example, three-dimensional FEM may be performed using the ANSYS Maxwell® simulation software. In one simulation, each of the three-dimensional models was partitioned into 1800000 or more tetrahedral elements.

Generally, simulation of neural activation requires accurate FEM results. Therefore, to ensure higher accuracy, a high resolution cylindrical region may be introduced around a fractal-based electrode. The high resolution cylindrical region may have, for example, a diameter of 40 mm and a height of 40 mm. A mesh size of less than 0.5 mm may be used.

The FEM solver in the simulation software may then be set to follow an adaptive iterative process such that an initial mesh can be seeded according to the geometrical derails of the structure. The Maxwell3D™ electrostatic solver may then compute and store a value for the electric potentials determined at the vertices and midpoints of the edges of each tetrahedron in the finite element mesh. The scalar potential field V may be calculated under a quasi-static assumption by solving the Laplace equation, $\nabla \cdot (\sigma \nabla V) = 0$, as well as calculating the electric field according to the equation, $E = -\nabla V$. After the electric field is determined, the Maxwell3D simulation software may provide solution files and an error analysis. In adaptive analysis, for example, the Maxwell3D solver may refine the tetrahedron associated with the highest error, and may then continue to solve until the stopping criterion is met. For example, the Maxwell3D solver may refine the mesh by 30% at each iteration and may proceed with each iteration until the difference between two successive solutions is less than 0.5% in the global energy error.

Neural activation may also be investigated through simulation models.

In one example simulation, the NEURON™ simulation environment may be used. For example, with the NEURON simulation environment, a population of 800 axons that are distributed in a cubic area of 4 cm×4 cm×2 cm above a fractal electrode may be modelled. The neurons may be modelled as 57 μm-diameter myelinated axons made of 21 nodes of Ranvier that are separated by 20 internodes. The potential distribution $V_0$ may be extracted from the above-described FEM model from a high-resolution cubic area located 15 mm above the surface of the planar electrode and applied as the extracellular potential to the electrical model of the axons. A 15 mm gap may be introduced to account for the presence of the peri-electrode space. The peri-electrode space is a region filled with extracellular fluid that is formed in the acute phase after electrode implantation.

Figure 5:
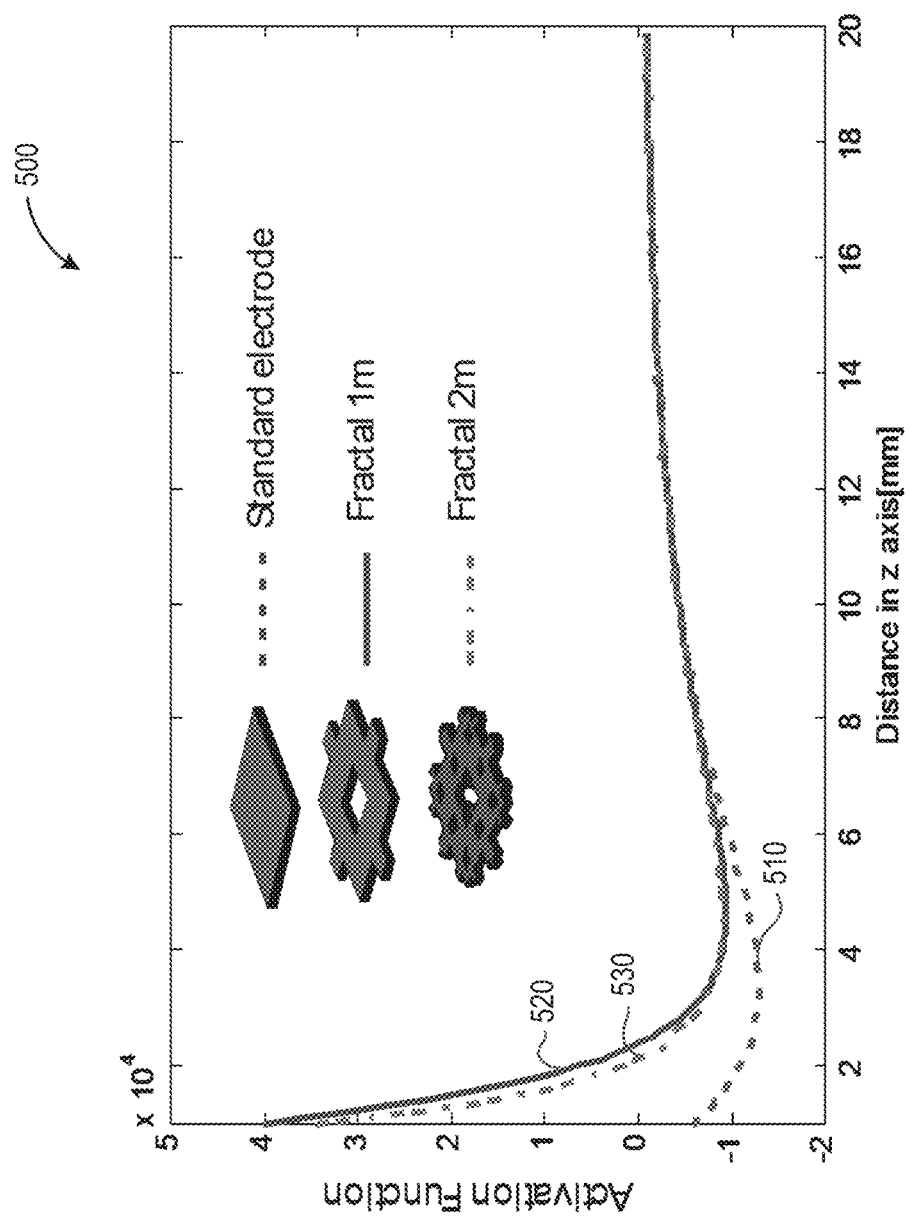
FIG. 5 is a graphical representation of simulation results of the neural activation function, in accordance with some embodiments.

For the purposes of comparison, a square-shaped electrode, a first order modified fractal electrode and a second order modified fractal electrode were modelled and simulated. The results from this simulation are generally illustrated in FIG. 5, which is a plot 500 associating neural activation function with distance along the z-axis (i.e., orthogonal to the surface of the electrode). It can be observed that the activation function 510 for the standard electrode exhibits small amplitude at the surface of the electrode and a diffuse effect within about 5 mm of the electrode surface. In contrast, the first and second order modified fractal electrodes, plotted as 520 and 530, respectively, achieve a comparatively high activation function value, with a steady drop-off up to about 5 mm from the electrode surface.

In particular, it can be observed that use of a fractal or modified fractal electrode results in an increase of neural activation function up to about a distance of 5 mm from a surface of the electrode. The absolute value of the increase in neural activation function relative to a conventional square electrode of equivalent surface area is increased between 2 and 10 times.

In the case of non-modified fractals, a similar increase in neural activation function has been observed within the first 5 mm of electrode surface, however the increase is more modest as lower effective current is delivered to the tissue.

Figure 6A:
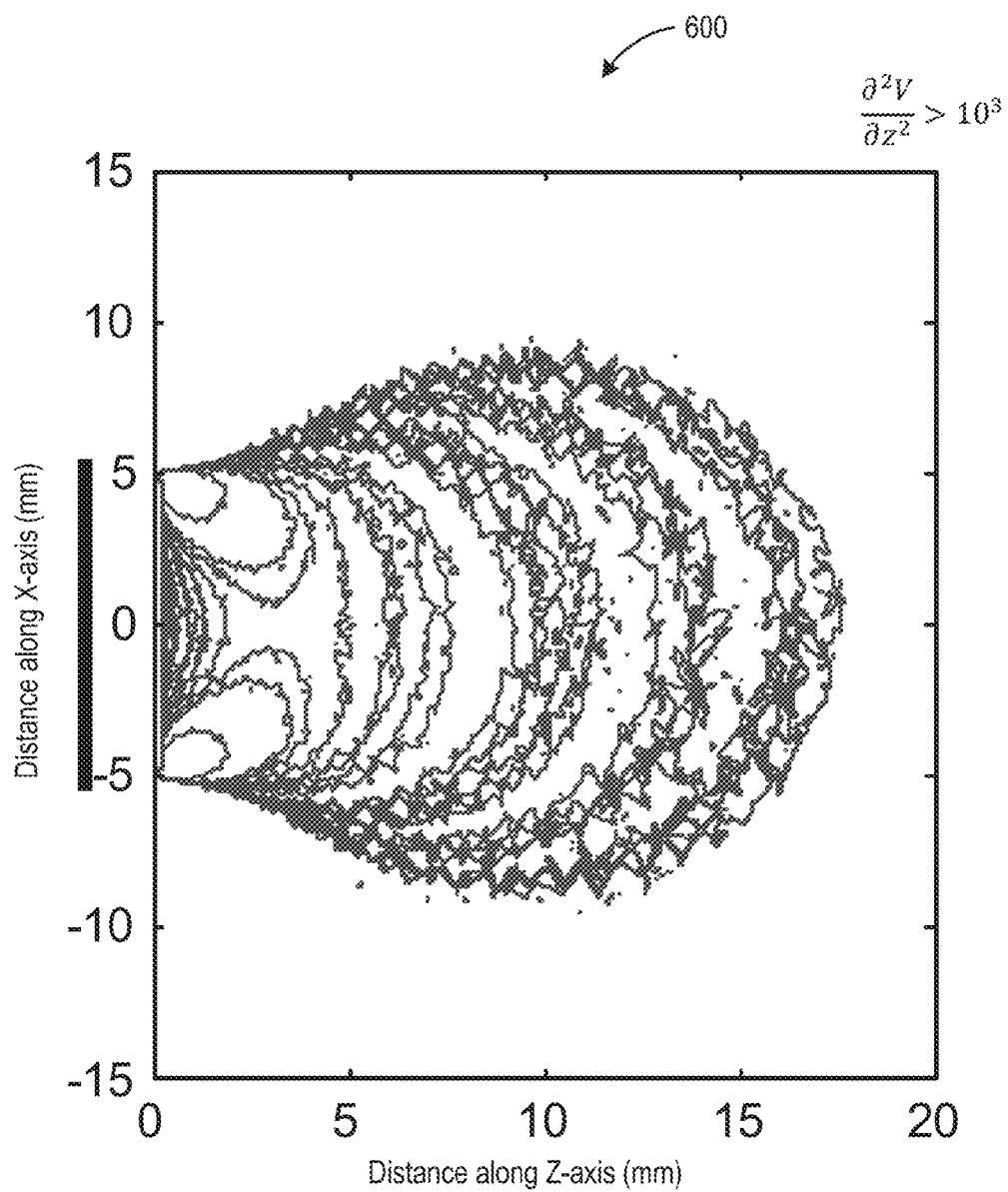
FIG. 6A is a graphical representation of a distribution of a second spatial derivative of an electric potential with respect to an axis perpendicular to a surface of a square electrode and in a plane orthogonal to the surface of the electrode.
Figure 6B:
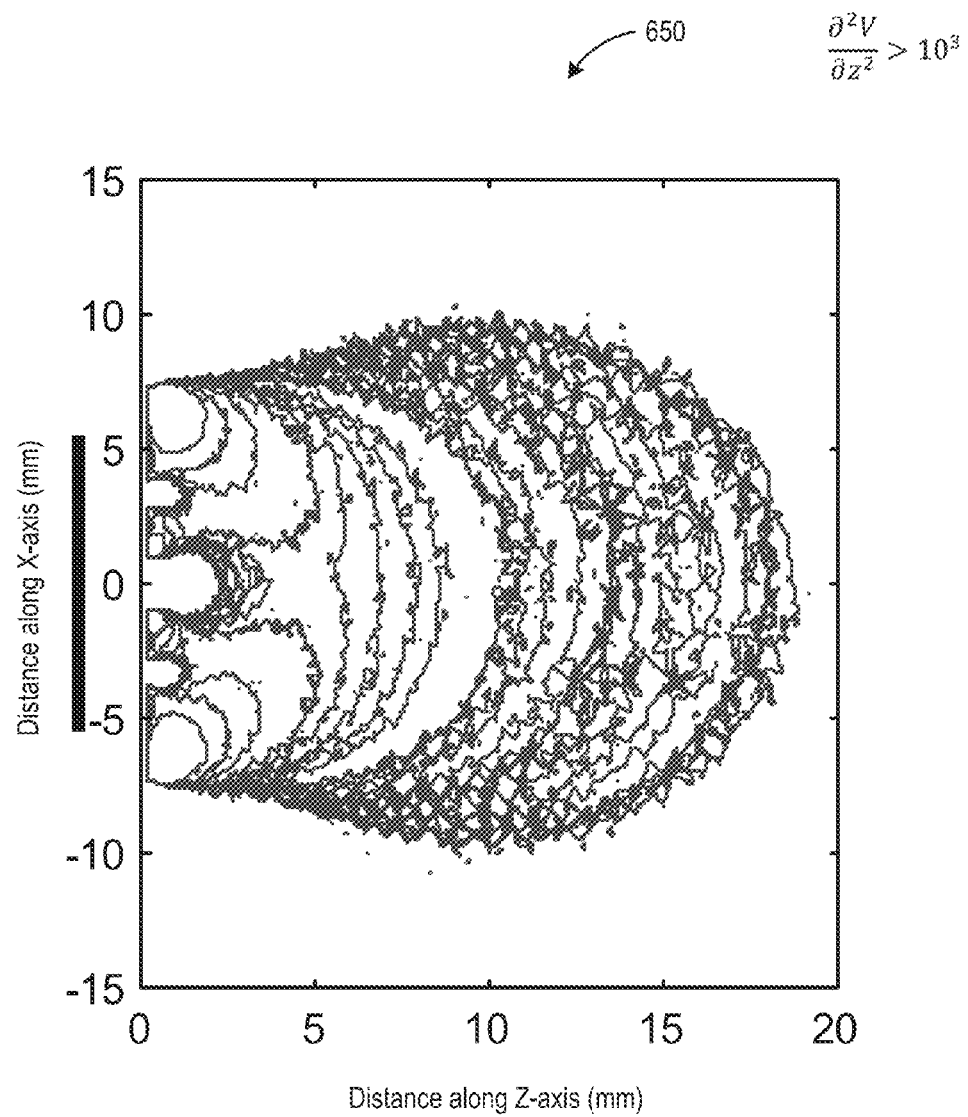
FIG. 6B is a graphical representation of a distribution of a second spatial derivative of an electric potential with respect to an axis perpendicular to a surface of a second order modified fractal electrode and in a plane orthogonal to the surface of the electrode.

Reference is now made to FIGS. 6A and 6B, in which there is illustrated the distribution of a second spatial derivative of the electric potential with respect to the z-axis in a plane orthogonal to the electrode surface. In particular, FIG. 6A illustrates the distribution of the second spatial derivative of the electric potential with respect to the z-axis in a plane orthogonal to the surface of a square electrode and FIG. 6B illustrates the distribution of the second spatial derivative of the electric potential with respect to the z-axis in a plane orthogonal to the surface of a second order modified fractal electrode.

As described above and shown in Equation (1), the neural activation function is directly proportional to the second spatial derivative of the electric potential with respect to the z-axis orthogonal to the surface of the electrodes. Generally, second derivatives of the electric potential with positive values can be used for denoting "depolarization" of axons while negative values can be used for denoting "hyperpolarization" of axons. By comparing the distribution of the second derivative of the electric potential in each of FIGS. 6A and 6B, it can be observed that the neural activation function in the tissue is improved when the second order modified fractal electrode is used. In particular, it can be observed that the contour lines for the modified electrode of FIG. 6B are denser and also broader, covering a larger area relative to the square electrode of FIG. 6A.

Figure 7:
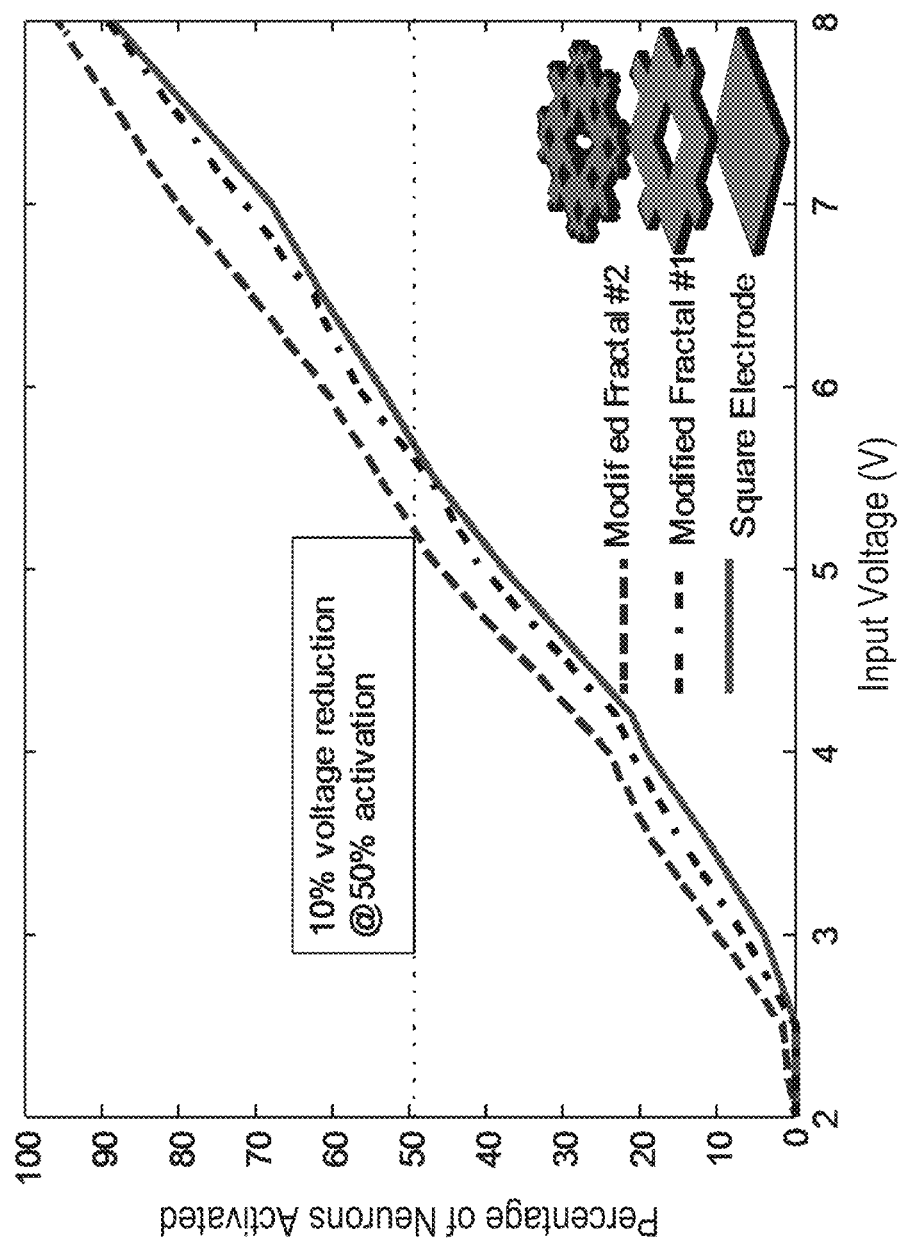
FIG. 7 is a graphical representation of a percentage of activated axons as a function of stimulus voltage amplitude.

Referring now to FIG. 7, there is illustrated an example graphical representation 700 of a percentage of activated axons as a function of stimulus voltage amplitude. As illustrated in FIG. 7, the use of a second order modified fractal electrode can decrease an average threshold voltage by 10% at the 50% activation level, as compared to a conventional square-shaped electrode.

Figure 8:
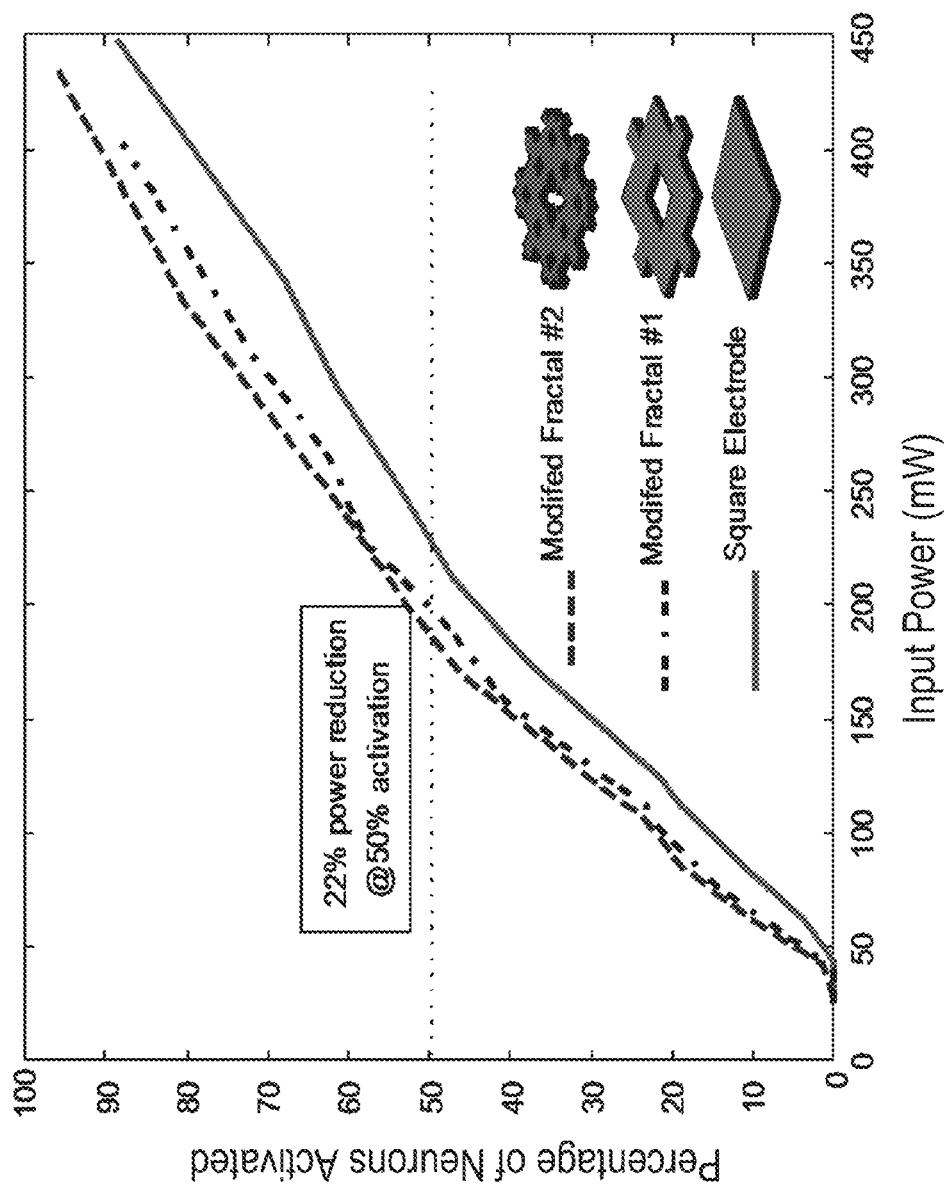
FIG. 8 is a graphical representation of a percentage of activated axons as a function of stimulus input power.

Referring now to FIG. 8, there is illustrated an example graphical representation 800 of a percentage of activated axons as a function of stimulus input power. As shown in FIG. 8, the use of a second order modified fractal electrode can decrease average power consumption by 22% at the 50% activation level, as compared to the conventional square-shaped electrode.

From FIGS. 7 and 8, it can also be observed that use of a first order modified fractal electrode can produce intermediate levels of improvement as compared to the conventional square-shaped electrode and second order modified fractal electrode.

Although the described embodiments have been described primarily in respect of planar electrodes, the described embodiments need not be limited to non-flexible, planar electrodes. In some embodiments, the described electrodes can be formed of flexible materials, or of stiffened materials that define a curved or rounded surface shape, to better conform to the target tissue.

Figure 9A:
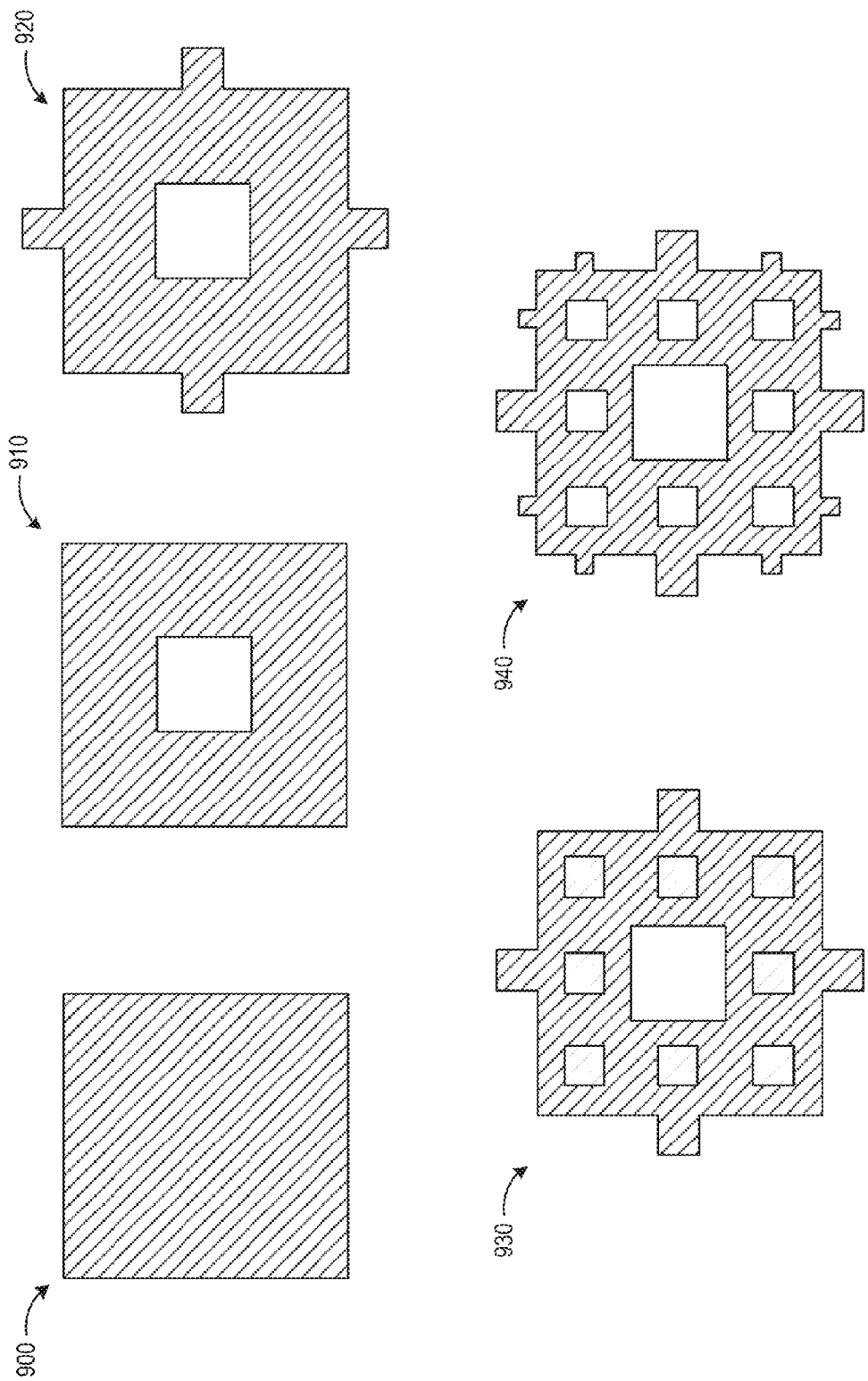
FIG. 9A provides plan views of electrodes used for in-vivo experiments.

To verify simulated results of electrode performance, in-vivo testing has been performed using several of the above-mentioned fractal electrode patterns. Referring now to FIG. 9A, there are illustrated plan views of five electrode shapes used for in-vivo testing.

Electrode 900 is a square planar electrode. Electrode 910 is a square electrode with a square center portion removed, similar to electrode 210 of FIG. 2B. Electrode 920 is an electrode with a modified fractal shape similar to electrode 230 of FIG. 2D. Electrodes 930 and 940 are still higher order modified fractal shapes.

Electrodes 900, 910, 920, 930 and 940 were fabricated in a laboratory using a "direct etch" technique. Patterns were transferred to a 1-sided, 4 mm (1/64") thick printed circuit board (PCB) with a FR-4 substrate and a 1 oz. copper layer. The electrodes were etched, cut into small PCB wafers and soldered with wires for use in electrical stimulation.

A subject was blinded to the test electrodes and tested for muscle activities evoked by stimulation with each of the electrodes. Electromyograms (EMGs) were recorded from the left abductor pollicis brevis (APB) muscle using a bipolar electrode configuration, in which the median nerve was stimulated at the wrist (cathode proximal) using a 200-μs square wave pulse. The test electrode was placed on the distal (anodal) part of the wrist over the median nerve, while a ground electrode was placed proximally along the median nerve.

Signals detected at the APB muscle were amplified 1000 times, bandpass filtered (between 5-500 Hz), digitized and recorded. The EMG signal was continuously monitored with visual and auditory feedback to ensure complete muscle relaxation.

Perceptual thresholds (PTs) were measured for each test electrode. Input and output curves were measured by recording the compound muscle action potentials from median nerve stimulation at twice the perceptual threshold. Ten compound muscle action potentials were recorded and averaged for each electrode, and the amplitudes were measured peak-to-peak.

Figure 9B:
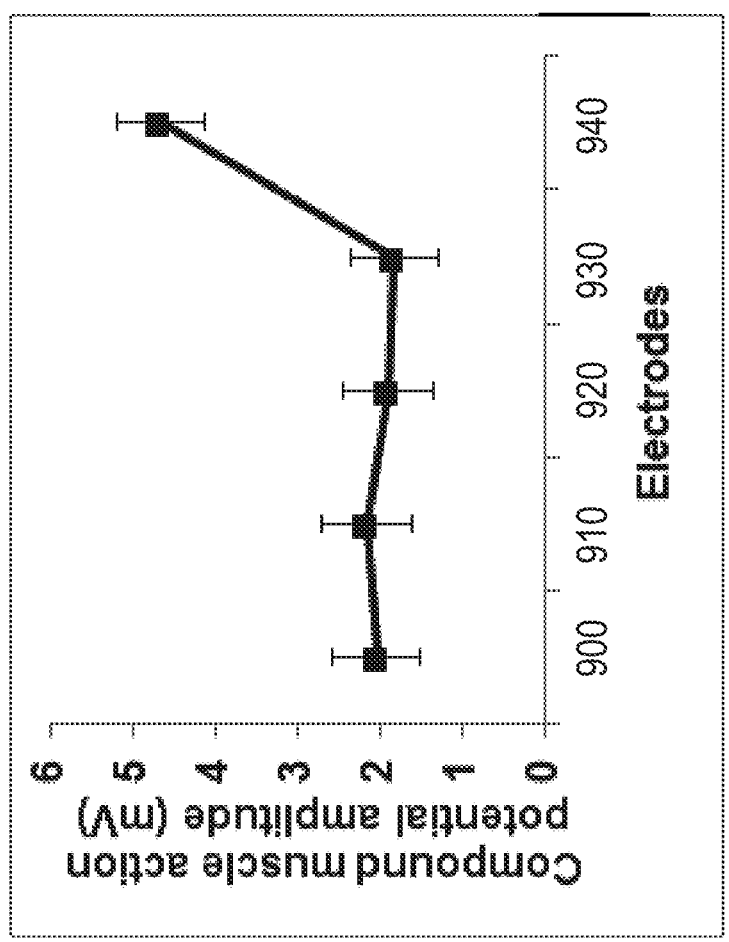
FIG. 9B illustrates measured potential amplitudes for the electrodes of FIG. 9A.

FIG. 9B illustrates the measured potential amplitudes for the electrodes of FIG. 9A. In particular, FIG. 9B illustrates the average and standard deviations of the amplitudes of compound muscle action potentials recorded from stimulation using each electrode.

Although the experimental results differed in some respects from simulated results, a positive trend in increasing muscle activity was confirmed for the second order modified electrode which was consistent with simulated input-output curves as in FIGS. 6 and 7.

FIGS. 9A and 9B illustrate experimental results for a single subject only. It is possible that differences between different fractal electrode types (as predicted by simulation described herein), can be captured only when larger groups of subjects are recruited and analysed. Another likely possibility is that improved procedures for fabricating the electrodes will be necessary to observe changes on in-vivo tests that are consistent with predictions. For example, the use of PCBs was expeditious for preliminary tests, but a) placed the electrodes at a distance from the skin surface; b) introduced an insulating material between the electrodes and the skin surface; and c) reduced the conductive contact between the electrode and the skin surface. These effects collectively reduced the ability of the prototype electrodes to stimulate the median nerve.

FIG. 10 illustrates one example curved profile electrode 1000 with third order modified fractal shape 1010, which conforms to a target tissue 1020 having a generally cylindrical shape.

Embodiments of the electrodes described herein may be used, for example, for neural stimulation. Specific examples of applications include ESCS, ECS, tDCS, and DBS. Embodiments may also be used for electrical stimulation of the bladder and related tissues, and in cardiac pacemaker applications.

The present invention has been described here by way of example only, while numerous specific details are set forth herein in order to provide a thorough understanding of the exemplary embodiments described herein. However, it will be understood by those of ordinary skill in the art that these embodiments may, in some cases, be practiced without these specific details. In other instances, well-known methods, procedures and components have not been described in detail so as not to obscure the description of the embodiments. Various modification and variations may be made to these exemplary embodiments without departing from the spirit and scope of the invention, which is limited only by the appended claims.

We claim:

1. An electrode for neural stimulation, the electrode comprising:
    an electrically conductive body, the body having a generally planar core portion,
    wherein the generally planar core portion has a plurality of holes therein, and wherein the plurality of holes has one or more internal perimeters,
    wherein each of the one or more internal perimeters comprises at least three edges and at least three vertices, each edge being joined to its adjacent edges at a respective one of the at least three vertices,
    wherein a shape of the generally planar core portion is obtainable from a base shape that corresponds to a regular polygon having n sides by:
        removing a first order smaller regular polygon having n sides from the interior of the base shape to provide a first order hole in the plurality of holes, the first order hole having n edges,
        dividing an area of the first order smaller regular polygon into a plurality of second order smaller regular polygons having n sides, and
        increasing a number of vertices of the shape by attaching the second order smaller regular polygons to one or more selected edges of the shape.

2. The electrode of claim 1, wherein the at least three edges define a non-180° angle at each vertex in the at least three vertices.

3. The electrode of claim 1, wherein respective edges and vertices of the plurality of holes are configured to reduce a capacity dimension of a surface of the core portion to less than 2.

4. The electrode of claim 1, wherein each of the one or more internal perimeters comprise at least twelve edges and at least twelve vertices.

5. The electrode of claim 4, wherein the plurality of holes form a Sierpinski triangle of at least order 2.

6. The electrode of claim 1, wherein each of the one or more internal perimeters comprise at least thirty-six edges and at least thirty-six vertices.

7. The electrode of claim 6, wherein the plurality of holes form a Sierpinski square of at least order 2.

8. The electrode of claim 1, wherein each of the plurality of holes has a perimeter shape that is self-similar to a perimeter shape of the generally planar core portion.

9. The electrode of claim 1, wherein the generally planar core portion has a base shape that corresponds to a regular polygon having n sides.

10. The electrode of claim 1, wherein the shape is further obtainable by removing a plurality of k-th order smaller regular polygons having n sides from the interior of the base shape to provide a plurality of k-th order holes in the plurality of holes, each of the plurality of k-th order holes having n edges.

11. The electrode of claim 10, wherein the shape is further obtainable by repeatedly removing the plurality of k-th order smaller regular polygons for two or more integer values of k.

12. The electrode of claim 10, wherein the shape is further obtainable by dividing an area of each of the plurality of k-th order smaller regular polygons to provide (k+1)-th order smaller regular polygons having n sides, and attaching the (k+1)-th order smaller regular polygons to an edge of the shape.

13. The electrode of claim 10, wherein k is between 2 and 5.

14. The electrode of claim 1, wherein n is at least 20, and wherein the generally planar core portion approximates a closed curve in shape.

15. The electrode of claim 1, wherein the generally planar core portion forms a closed curve in shape, and wherein each of the plurality of holes forms a closed curve in shape.

16. The electrode of claim 1, wherein a shape of the generally planar core portion is obtainable from a base shape that corresponds to a closed curve by removing a first order smaller closed curve from the interior of the base shape to provide a first order hole in the plurality of holes.

17. The electrode of claim 16, wherein the shape is further obtainable by removing a plurality of k-th order smaller closed curves from the interior of the base shape to provide a plurality of k-th order holes in the plurality of holes.

18. The electrode of claim 17, wherein the shape is further obtainable by repeatedly removing the plurality of k-th order smaller closed curves for two or more integer values of k.

19. The electrode of claim 1, wherein the generally planar core portion is curved.

20. The electrode of claim 1, wherein the generally planar core portion is flexible.

21. The electrode of claim 1, wherein the one or more selected edges of the shape comprise at least one external perimeter edge of the generally planar core portion, and wherein attaching the second order smaller regular polygons to one or more selected edges of the shape.

22. The electrode of claim 1, wherein the one or more selected edges of the shape comprise at least one of the at least three edges of the one or more internal perimeters.

* * * * *